(12) United States Patent
Smith et al.

(10) Patent No.: US 10,589,124 B2
(45) Date of Patent: Mar. 17, 2020

(54) INTEGRATED HIGH-RESOLUTION UNTETHERED FLEXIBLE NEURAL IMPLANT

(71) Applicant: ARIZONA BOARD OF REGENTS ON BEHALF OF ARIZONA STATE UNIVERSITY, Scottsdale, AZ (US)

(72) Inventors: Joseph Smith, Tempe, AZ (US); Barry O'Brien, Chandler, AZ (US); Yong-Kyun Lee, Chandler, AZ (US); Edward Bawolek, Chandler, AZ (US); Jennifer Blain Christen, Chandler, AZ (US); Michael Goryll, Mesa, AZ (US); Jitendran Muthuswamy, Chandler, AZ (US); George R. Kunnen, Chandler, AZ (US); David Allee, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 332 days.

(21) Appl. No.: 15/111,952

(22) PCT Filed: Jan. 13, 2015

(86) PCT No.: PCT/US2015/011092
§ 371 (c)(1),
(2) Date: Jul. 15, 2016

(87) PCT Pub. No.: WO2015/156862
PCT Pub. Date: Oct. 15, 2015

(65) Prior Publication Data
US 2016/0331994 A1    Nov. 17, 2016

Related U.S. Application Data

(60) Provisional application No. 61/928,170, filed on Jan. 16, 2014.

(51) Int. Cl.
*A61N 5/06* (2006.01)
*A61B 5/04* (2006.01)

(52) U.S. Cl.
CPC ........ *A61N 5/0622* (2013.01); *A61B 5/04001* (2013.01); *A61N 5/0601* (2013.01);
(Continued)

(58) Field of Classification Search
CPC ................ A61N 5/0622; A61N 5/0601; A61N 2005/0612; A61N 2005/0626;
(Continued)

(56) References Cited

U.S. PATENT DOCUMENTS 9,180,309 B2 * 11/2015 Nirenberg .............. G06K 9/605
9,302,103 B1 *  4/2016 Nirenberg .......... A61N 1/36067
(Continued)

FOREIGN PATENT DOCUMENTS

WO    2013046113 A1    4/2013
WO    2013142196 A1    9/2013

OTHER PUBLICATIONS

Foutz et al, "Theoretical principles underlying optical stimulation of a channelrhodopsin-2 positive pyramidal neuron," J. Neurophysiol, vol. 107, pp. 3235-3245, 2012.
(Continued)

*Primary Examiner* — Lynsey C Eiseman
*Assistant Examiner* — Amanda L Steinberg
(74) *Attorney, Agent, or Firm* — Quarles & Brady LLP; James M. Schleicher

(57) ABSTRACT

Systems and methods for stimulating neural tissue are disclosed. An array of optically emissive pixels is configured to deliver light to the neural tissue of a subject. Individual pixels within the array can be addressed to selectively illuminate a portion of the neural tissue when a neurological event occurs. The system can also include an array of
(Continued)

microelectrodes in electrical communication with the array of pixels and a power source. A biocompatible substrate can be used to support the microelectrodes pixels, and the power source. A microelectrode circuit and a pixel circuit can also be supported by the biocompatible substrate.

13 Claims, 13 Drawing Sheets

(52) U.S. Cl.
CPC ............... *A61N 2005/0612* (2013.01); *A61N 2005/0626* (2013.01); *A61N 2005/0653* (2013.01); *A61N 2005/0663* (2013.01)

(58) Field of Classification Search
CPC .... A61N 2005/0653; A61N 2005/0663; A61B 5/04001
USPC ..................................................... 607/88–94
See application file for complete search history.

(56) References Cited

U.S. PATENT DOCUMENTS

| | | | |
|---|---|---|---|
| 2005/0099824 A1* | 5/2005 | Dowling | A61B 1/0653 362/572 |
| 2010/0217341 A1 | 8/2010 | John et al. | |
| 2010/0249890 A1 | 9/2010 | Choi et al. | |
| 2011/0127405 A1 | 6/2011 | Grossman et al. | |
| 2012/0253261 A1 | 10/2012 | Poletto et al. | |

OTHER PUBLICATIONS

Deisseroth, "Controlling the Brain with Light," Scientific American, vol. 303, pp. 48-55, Nov. 2010.
Zhang et al, "Multimodal fast optical interrogation of neural circuitry," Nature, vol. 446, pp. 633-639, 2007.
Han et al, "Multiple Color Optical Activation, Silencing, and Desynchronization of Neural Activity with Single Spike Temporal Resolution," PLoS One, Issue 3, pp. 1-12, Mar. 2007.
Wang et al, "Integrated Device for combined optical neuromodulation and electrical recording for chronic in vivo applications," Journal of Neural Engineering, vol. 9, pp. 1-14, 2012.
Kim et al, "Waterproof AlInGaP Optoelectronics on stretchable substrates with applications in biomedicine and robotics," Nature Materials, vol. 9, pp. 929-937, 2010.
O'Brien et al, "14.7" Active Matrix PHOLED Displays on Temporary Bonded PEN Substrates with Low Temperature IGZO TFTs, SID Symposium Digest of Technical Papers, vol. 70.2L, pp. 447-450, 2013.
Feili et al, "Flexible microelectrode arrays with integrated organic semiconductors," 9th Annual conference of the International FES Society, 3 pp., 2004.
Sarma et al, "Active Matrix OLED Using 150C a-Si TFT Backplane Built on Flexible Plastic Substrate," Proc. of SPIE, vol. 5080, pp. 180-191, 2003.
Marrs et al, "Control of Threshold Voltage and Saturation Mobility Using Dual Active Layer Device Based on Amorphous Mixed Metal-Oxide-Semiconductor on Flexible Plastic Substrates," IEEE Transactions on Electron Devices, vol. 58, No. No. 10, pp. 3428-3434, Oct. 2011.
Venugopal et al, "Flexible Electronics: What can it do? What should it do?," Reliability Physics Symposium, vol. 2010, IRPS10-644 to IRPS10-648, May 2010.
Smith et al, "Flexible Digital x-ray technology for far-forward remote diagnostic and conformal x-ray imaging applications," Proc. of SPIE, vol. 8730, pp. 87300E-1 thru 87300E-7, 2013.
Forrest et al, "Measuring the Efficiency of Organic Light Emitting Devices," Advanced Materials, vol. 15, No. 13, pp. 1043-1048, 2013.

Ohmori et al, "Realization of Polymeric Optical Integrated Devices Utilizing Organic Light Emitting Diodes and Photodetectors Fabricated on a Polymeric Waveguide," IEEE Journal of Selected Topics in Quantum Electronics, vol. 10, No. 1, pp. 70-78, 2004.
Huang et al, "Optogenetic Investigation of Neuropsychiatric Diseases," International Journal of Neuroscience, vol. 123, No. 1, pp. 7-16, Jan. 2013.
Tourino et al, "Optogenetics in psychiatric diseases," Current Opinion in Neurobiology, vol. 23, No. 3, pp. 430-435, Jun. 2013.
Bentley et al, "Optogenetics in epilepsy," Neurosurgical Focus, vol. 34, No. 6, pp. 1-5, Jun. 2013.
Kokaia et al, "An optogenetic approach in epilepsy," Neuropharmacology, vol. 69, pp. 89-95, Jun. 2013.
Xie et al, "Resistance of optogenetically evoked motor function to global ischemia and reperfusion in mouse in vivo," Journal of Cerebral Blood Flow and Metabolism, vol. 33, No. 8, pp. 1148-1152, Aug. 2013.
Paz et al, "Closed-loop optogenetic control of thalamus as a tool for interrupting seizures after cortical injury," Nature Neuroscience, vol. 16, No. 1, pp. 64-70, Jan. 2013.
Wang et al, "Optogenetic dissection of cortical information processing-shining light on schizophrenia," Brain Research, vol. 1476, pp. 31-37, Oct. 2012.
Bell et al, "Nicotinic excitatory postsynaptic potentials in hippocampal CA1 interneurons are predominantly mediated by nicotinic receptors that contain alpha 4 and beta 2 subunits," Neuropharmacology, vol. 61, No. 8, pp. 1379-1388, Dec. 2011.
Sridharan et al, "Voltage Preconditioning Allows Modulated Gene Expression in Neurons Using PEI-complexed siRNA," Mol Ther Nucleic Acids, vol. 2, pp. e82, 12 pp., 2013.
O'Brien et al, "White Organic Light Emitting Diodes using Pt-Based Red, Green, and Blue Phosphorescent Dopants," Proc. of SPIE, vol. 8829, pp. 882909-1 thru 882909-6, 2013.
Nakanotani et al, "Promising operational stability of high-efficiency organic light-emitting diodes based on thermally activated delayed fluorescence," Scientific Reports, vol. 3, pp. 1-5, 2013.
Herman et al, "Fabrication and characterization of a silicone fluorescent oxygen sensor." IEEE Biomedical Circuits and Systems Conference, BioCAS, pp. 70-73, 2010.
Kargar et al, "Theoretical investigation of silicon nanowire pH sensor." Proceedings of the 2nd Biennial IEEE/RAS-EMBS International Conference on Biomedical Robotics and Biomechatronics Scottsdale, AZ, USA, Oct. 19-22, pp. 765-769, 2008.
Welch et al, "An optoelectronic/microfluidic inclination sensor for vestibular implants." IEEE Biomedical Circuits and Systems Conference (BioCAS 2009), pp. 281-284, Nov. 26-28, 2009.
Welch et al, "A multiparametric biosensor array for on-chip cell culture with feedback controlled microfluidics." 2011 IEEE International Symposium of Circuits and Systems (ISCAS), pp. 809-812, May 2011.
Welch et al, "On-chip cell culture biosensing with microfluidic feedback control." In Life Science Systems and Applications Workshop (LiSSA), IEEE/NIH, pp. 39-42, 2011.
Welch et al, "Experimental and Simulated Cycling of ISFET Electric Fields for Drift Reset," Electron Device Letters, IEEE, vol. 34, No. 3, pp. 456-458, 2013.
Welch et al, "Fully differential current-mode MEMS dual-axis optical inclination sensor," Sensors and Actuators A: Physical, vol. 192, pp. 133-139, Apr. 2013.
Andreou et al, "Contactless fluorescence imaging with a CMOS image sensor." 2011 IEEE International Symposium an Circuits and Systems (ISCAS), pp. 2341-2344, May 2011.
Christen et al, "A Self-Biased Operational Transconductance Amplifier in 0.18 micron 3D SOI-CMOS." 2007 IEEE International Symposium on Circuits and Systems, ISCAS, pp. 137-140, 2007.
Song et al, "Amplification circuit and microelectrode array for HL-1 Cardiomyocyte action potential measurement." 2010 IEEE International Symposium on Circuits and Systems (ISCAS), pp. 1384-1387, May 2010.
Song et al, "A fully-adjustable dynamic range capacitance sensing circuit in a 0.15μm 3D SOI process." 2011 IEEE International Symposium on Circuits and Systems (ISCAS), pp. 1708-1711, May 2011.

(56) References Cited

OTHER PUBLICATIONS

Welch et al, "CMOS biosensor system for on-chip cell culture with read-out circuitry and microfluidic packaging." 34th Annual International Conference of the IEEE Engineering in Medicine and Biology Society, pp. 4990-4993, Aug. 2012.

Christen et al, "Localized closed-loop temperature control and regulation in hybrid silicon/silicone life science microsystems." 2007 IEEE International Symposium on Circuits and Systems (ISCAS), pp. 2886-2889, May 2007.

Christen et al, "Design, double sided post-processing, and packaging of CMOS compatible bio-MEMS device arrays" IEEE International Symposium on Circuits and Systems, ISCAS, pp. I-665-I-668, 2002.

Christen et al, "CMOS heater array for incubation environment cellular study." 48th Midwest Symposium on Circuits and Systems, vol. 2, pp. 1786-1789, 2005.

Christen et al, "Integrated PDMS/CMOS Microsystem for Autonomous Incubation and Imaging in Cell Culture Studies." 2006 IEEE/NLM Life Science Systems and Applications Workshop, pp. 1-2, 2006.

Christen et al, "Hybrid Silicon/Silicone (polydimethylsiloxane) Microsystem for Cell Culture." 2006 IEEE International Symposium on Circuits and Systems, pp. 1135-1138, May 2006.

Christen et al, "Design, Analysis and Implementation of Integrated Micro-Thermal Control Systems." 2007 IEEE International Symposium on Circuits and Systems, pp. 2011-2014, May 2007.

Christen et al, "Design, Fabrication, and Testing of a Hybrid CMOS/PDMS Microsystem for Cell Culture and Incubation," IEEE Transactions on Biomedical Circuits and Systems, vol. 1, No. 1, pp. 3-18, 2007.

Qiu et al, "Reactive nanolayers for physiologically compatible microsystem packaging," Journal of Materials Science-Materials in Electronics, vol. 21, No. 6, pp. 562-566, Jun. 2010.

Welch et al, "Seamless integration of CMOS and microfluidics using flip chip bonding," Journal of Micromechanics and Microengineering, vol. 23, No. 3, 035009, 7 pp., Mar. 2013.

Jain et al, "Bio-chip for spatially controlled transfection of nucleic acid payloads into cells in a culture," Lab on a Chip, vol. 7, No. 8, pp. 1004-1011, 2007.

Jain et al, "Microsystem for transfection of exogenous molecules with spatio-temporal control into adherent cells," Biosensors & Bioelectronics, vol. 22, No. 6, pp. 863-870, Jan. 2007.

Jain et al, "Microelectrode array (MEA) platform for targeted neuronal transfection and recording," IEEE Transactions on Biomedical Engineering, vol. 55, No. 2, pp. 827-832, Feb. 2008.

Khraiche et al, "Multi-modal biochip for simultaneous, real-time measurement of adhesion and electrical activity of neurons in culture," Lab on a Chip, vol. 12, No. 16, pp. 2930-2941, 2012.

Muthuswamy et al, "An array of microactuated microelectrodes for monitoring single-neuronal activity in rodents," IEEE Transactions on Biomedical Engineering, vol. 52, No. 8, pp. 1470-1477, Aug. 2005.

Muthuswamy et al, "Single neuronal recordings using surface micromachined polysilicon microelectrodes," Journal of Neuroscience Methods, vol. 142, No. 1, pp. 45-54, Mar. 2005.

Saha et al, "Structure-property relationships in the optimization of polysilicon thin films for electrical recording/stimulation of single neurons," Biomedical Microdevices, vol. 9, No. 3, pp. 345-360, Jun. 2007.

Saha et al, "Highly Doped Polycrystalline Silicon Microelectrodes Reduce Noise in Neuronal Recordings In Vivo," IEEE Transactions on Neural Systems and Rehabilitation Engineering, vol. 18, No. 5, pp. 489-497, Oct. 2010.

Sridharan et al, "Immobilization of functional light antenna structures derived from the filamentous green bacterium Chloroflexus aurantiacus," Langmuir, vol. 24, No. 15, pp. 8078-8089, Aug. 2008.

Sridharan et al, "Optoelectronic Energy Transfer at Novel Biohybrid Interfaces Using Light Harvesting Complexes from Chloroflexus aurantiacus," Langmuir, vol. 25, No. 11, pp. 6508-6516, Jun. 2009.

Anand et al, "Electrothermal Microactuators With Peg Drive Improve Performance for Brain Implant Applications," Journal of Microelectromechanical Systems, vol. 21, No. 5, pp. 1172-1186, Oct. 2012.

Jackson et al, "Artificial dural sealant that allows multiple penetrations of implantable brain probes," Journal of Neuroscience Methods, vol. 171, No. 1, pp. 147-152, Jun. 2008.

Jackson et al, "Flexible Chip-Scale Package and Interconnect for Implantable MEMS Movable Microelectrodes for the Brain," Journal of Microelectromechanical Systems, vol. 18, No. 2, pp. 396-404, Apr. 2009.

Muthuswamy et al, "Electrostatic microactuators for precise positioning of neural microelectrodes," IEEE Transactions on Biomedical Engineering, vol. 52, No. 10, pp. 1748-1755, Oct. 2005.

Sutanto et al, "Novel First-Level Interconnect Techniques for Flip Chip on MEMS Devices," Journal of Microelectromechanical Systems, vol. 21, No. 1, pp. 132-144, Feb. 2012.

Sutanto et al, "Packaging and Non-Hermetic Encapsulation Technology for Flip Chip on Implantable MEMS Devices," Journal of Microelectromechanical Systems, vol. 21, No. 4, pp. 882-896, Aug. 2012.

Gilletti et al, "Brain micromotion around implants in the rodent somatosensory cortex," Journal of Neural Engineering, vol. 3, No. 3, pp. 189-195, Sep. 2006.

Jackson et al, "Nonhermetic Encapsulation Materials for MEMS-Based Movable Microelectrodes for Long-Term Implantation in the Brain," Journal of Microelectromechanical Systems, vol. 18, No. 6, pp. 1234-1245, Dec. 2009.

Muthuswamy et al, "Vulnerability of the thalamic somatosensory pathway after prolonged global hypoxic-ischemic injury," Neuroscience, vol. 115, No. 3, pp. 917-929, 2002.

Stice et al, "Thin microelectrodes reduce GFAP expression in the implant site in rodent somatosensory cortex," Journal of Neural Engineering, vol. 4, No. 2, pp. 42-53, Jun. 2007.

Stice et al, "Assessment of gliosis around moveable implants in the brain," Journal of Neural Engineering, vol. 6, No. 4, 046004 (10pp), Aug. 2009.

Packer et al, "Targeting neurons and photons for optogenetics," Nature Neuroscience, vol. 16, No. 7, pp. 805-815, Jul. 2013.

Miyashita et al, "Long-term channelrhodopsin-2 (ChR2) expression can induce abnormal axonal morphology and Iargeting in cerebral cortex," Frontiers in Neural Circuits, vol. 7, Article 8, 10 pp., Jan. 2013.

Cardin, "Dissecting local circuits in vivo: Integrated optogenetic and electrophysiology approaches for exploring inhibitory regulation of cortical activity," Journal of Physiology-Pads, vol. 106, No. 3-4, pp. 104-111, May-Aug. 2012.

Yawo et al, "Optogenetic manipulation of neural and non-neural functions," Development Growth & Differentiation, vol. 55, No. 4, pp. 474-490, May 2013.

Christen et al, "Ultra-high ratio dilution microfluidic system for single strand DNA isolation." 2008 IEEE International Symposium on Circuits and Systems, pp. 1822-1825, May 2008.

Ordonez et al, "Thin films and microelectrode arrays for neuroprosthetics," MRS Bulletin, vol. 37, pp. 590-598, 2012.

Iyer et al, "Virally mediated optogenetic excitation and inhibition of pain in freely moving nontransgenic mice," Nat Biotechnol., vol. 32, pp. 274-278, 2014.

Huston et al., "The pulse of inflammation: heart rate variability, the cholinergic anti-inflammatory pathway and implications for therapy," Journal of Internal Medicine, 269(1):45-53, Jan. 2011.

Tracey, The inflammatory reflex, Nature, 420(6917):853-859, Dec. 2002.

Henry, Therapeutic mechanisms of vagus nerve stimulation, Neurology, 59(Suppl 4):S3-S14, Sep. 2002.

Rong et al., Transcutaneous vagus nerve stimulation for the treatment of depression: A study protocol for a double blinded randomized clinical trial, BMC Complementary and Alternative Medicine, 12(1):255, pp. 1-6, Dec. 2012.

Frangos et al., Non-invasive Access to the Vagus Nerve Central Projections via Electrical Stimulation of the External Ear: fMRI Evidence in Humans, Brain Stimulation, 8(3):624-636, May 2015.

Deisseroth, Optogenetics, Nature Methods, 8(1):26-29, Jan. 2011.

(56) References Cited

OTHER PUBLICATIONS

Smith et al., Application of Flexible OLED Display Technology for Electro-Optical Stimulation and/or Silencing of Neural Activity, Journal of Display Technology, 10(6):514-520, 2014.
Lochner et al., All-organic optoelectronic sensor for pulse oximetry. Nature Communications, 5:5745(1-7), Dec. 2014.
Kim et al., Injectable, cellular-scale optoelectronics with applications for wireless optogenetics, Science, 340 (6129):211-216, Apr. 2013.
Degenaar et al., Individually addressable optoelectronic arrays for optogenetic neural stimulation., 2010 Biomedical aircuits and Systems Conference (BioCAS), pp. 170-173, 2010.
Wilkinson et al., Enhanced performance of pulse driven small area polyfluorene light emitting diodes., Applied Physics Letters, 79(2):171-173, Jul. 2001.
Nakanotani et al., Injection and Transport of High Current Density over 1000 A/cm2 in Organic Light Emitting Diodes under Pulse Excitation., Japanese Journal of Applied Physics, 44(6A):3659-3662, Jun. 2005.
Eversmann et al., A 128 × 128 CMOS biosensor array for extracellular recording of neural activity., IEEE Journal of Solid-State Circuits, 38(12):2306-2317, Dec. 2003.
Smith et al., Flexible ISFET Biosensor Using IGZO Metal Oxide TFTs and an ITO Sensing Layer., IEEE Sensors Journal, 14(4):937-938, 2014.
Allen, Photoplethysmography and its application in clinical physiological measurement., Physiological Measurement, 28(3):R1-R39, Mar. 2007.
Suzuki et al, Development of the irregular pulse detection method in daily life using wearable photoplethysmographic sensor., 31st Annual International Conference of the IEEE Engineering in Medicine and Biology Society, pp. 5080-6083, 2009.
Schafer et al, How accurate is pulse rate variability as an estimate of heart rate variability? A review on studies aomparing photoplethysmographic technology with an electrocardiogram., International Journal of Cardiology,166 (1):15-29, Jun. 2013.
Tracey, Shock Medicine: Stimulation of the nervous system could replace drugs for inflammatory and autoimmune conditions., Scientific American, Mar. 2015, 312(3):28-35.
Darpa, ElectRx Has the Nerve to Envision Revolutionary Therapies for Self-Healing, Darpa.mil, <http://www.darpa.mil/news-events/2014-12-11>, Dec. 11, 2014.
Sudmundsson, Intracranial Pressure and the Role of the Vagus Nerve: A Hypothesis., World Journal of Neuroscience, 4:164-169, 2014.
Smith et al., Optogenetic Neurostimulation of the Auricular Vagus using Flexible OLED Display Technology to Treat Chronic Inflammatory Disease and Mental Health Disorders., Electronic Letters, 52(11):900-902, May 2016.
Raupp et al., Low-temperature amorphous-silicon backplane technology development for flexible displays in a manufacturing pilot-line environment., Journal of the Society for Information Display, 15(7):445-454, Jul. 2007.
Haq et al., Temporary bond-debond process for manufacture of flexible electronics: Impact of adhesive and carrier properties on performance., Journal of Applied Physics, 108(11)114917(1-7), 2010.
Wagner et al., Materials for stretchable electronics., MRS Bulletin, 37(3):207-213, Mar. 2012.
Klapoetke et al, Independent optical excitation of distinct neural populations., Nature Methods, 11(3):338-346, Mar. 2014.
Lin, "Optogenetic excitation of neurons with channelrhodopsins: Light instrumentation, expression systems, and channelrhodopsin variants," Progress in Brain Research, vol. 196, pp. 29-47, 2012.
Sridharan, et al., "Targeted Modulation of BACE1 Expression and Electrical Activity in Neuronal Cultures Using Voltage Pre-Conditioning," Molecular Therapy, vol. 21, Supplement 1, pp. S41-S41, May 2013.
International Search Report for PCT/US15/11092 dated Mar. 29, 2016.

\* cited by examiner

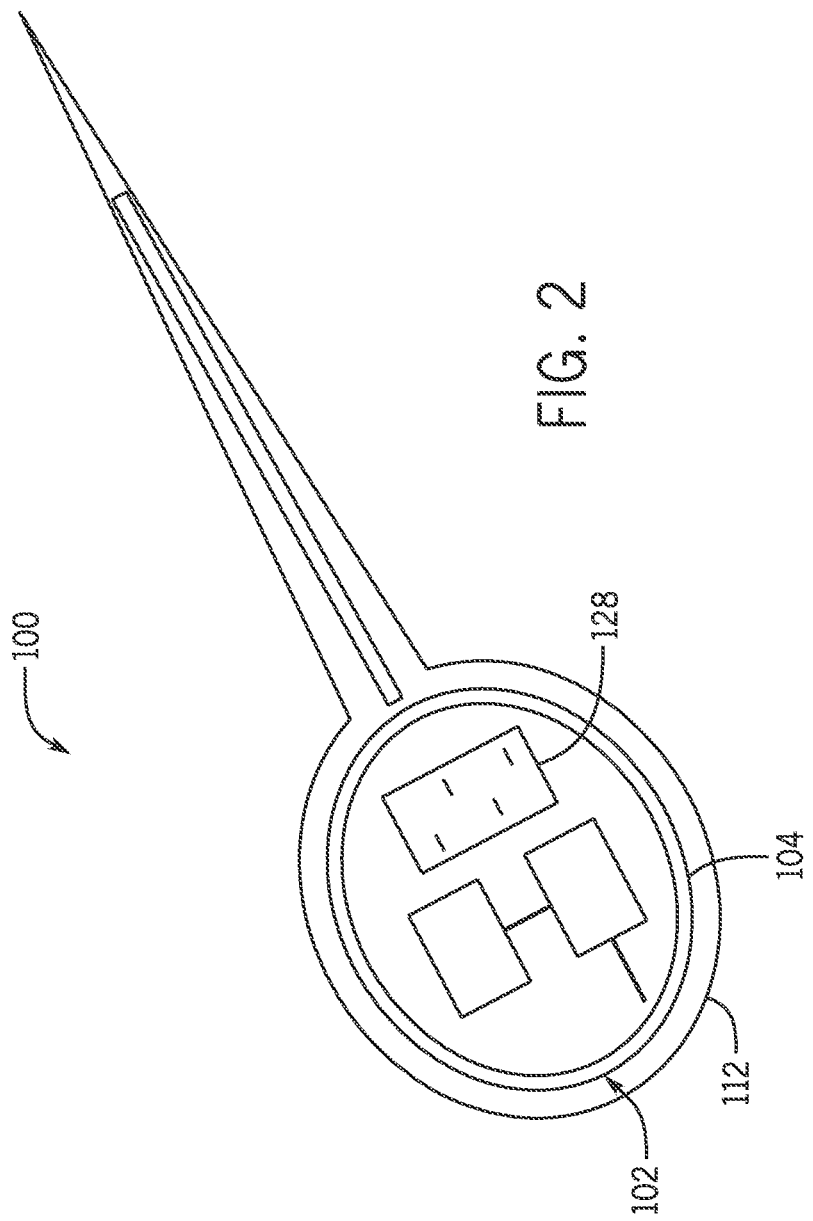

INTEGRATED HIGH-RESOLUTION UNTETHERED FLEXIBLE NEURAL IMPLANT

CROSS-REFERENCE TO RELATED APPLICATIONS

This application represents the nation stage entry of the PCT International Application No. PCT/US2015/011092 filed Jan. 13, 2015, which claims priority to U.S. Provisional Patent Application No. 61/928,170 filed Jan. 16, 2014, the disclosures of which are incorporated by reference herein by reference in their entirety for all purposes.

STATEMENT REGARDING FEDERALLY SPONSORED RESEARCH

This invention was made with government support under W911NF-04-2-0005 awarded by the Army Research Office. The government has certain rights in the invention.

BACKGROUND OF THE INVENTION

The field of the invention is cortical implants. More particularly, the invention relates to high-resolution, untethered flexible cortical implants.

Optogenetics, which uses light stimulation to control the excitation, inhibition, or signaling pathways of optically excitable cells in genetically modified neural tissue, provides a powerful tool to diagnose and treat, as well as understand, numerous neurological and psychiatric diseases and disorders such as epilepsy, stroke, seizures, paralysis, depression, schizophrenia, Parkinson's disease, and Alzheimer's disease. Using a viral vector, neurons are genetically modified to express light-gated ion channels in the cellular membrane sensitive to incident light. Cells expressing Channelrhodopsin-2 (ChR2) are activated or excited by blue light, while yellow light directed on cells that express Halorhodopsin are quieted or silenced.

Optogenetics may be divided into two different methodologies for neurological optical stimulation. One approach requires inserting the exposed tip of a fiber optic cable(s) into brain tissue. An external light source, either a laser or light-emitting diode (LED), is then mechanically connected to the unexposed end of the fiber-optic cable, and the neural tissue, both surrounding and underneath the exposed tip, is illuminated. Adding a connector to the short length of fiber-optic cable protruding from the cranial insertion point provides reasonable freedom of movement when the light source is not attached and activated. However, penetrating fiber-optic-based neural stimulation methods still require a permanent opening in the cranium, which poses serious infection risk. Additionally, the single cylindrical fiber light source from the exposed tip projects non-specific omnidirectional illumination over a large volume of neural tissue. Thus, the ability of fiber-optic-based methods to target specific neural regions is limited.

One solution to the fiber optic related limitations described above includes inserting a small array of discrete LEDs bonded to the surface of a mechanically compliant thin biocompatible substrate, which also provides the necessary electrical interconnections. Assuming a suitable miniature electrical power source for the LEDs can be mounted inside the skull, this approach is designed to eliminate the need for the permanent opening, as well as provide more directional and localized illumination. The array of sub-cranial LEDs can then be placed in direct contact with either the cortical surface or the deep brain using a penetrating probe with a smaller linear LED array. The surface-mounted, flexible, discrete LED array is designed to conform to the uneven or folded surface structures of the cerebral cortex for direct optical stimulation, or can be positioned in the narrow and deep crevice which separates the forebrain into its left and right cerebral hemispheres.

There are assumed to be significant clinical advantages to selectively (optically) exciting small isolated regions of neural tissue, as opposed to activating an entire emissive array. However, discrete LED-based methods are limited in resolution given the requirement to individually bond each discrete LED to the supporting flexible substrate, which quickly becomes unmanageable as the resolution is increased. More importantly, as the LED array size (i.e., x-y matrix resolution) increases beyond a few LEDs, the ability to individually activate each discrete LED is no longer possible unless a major portion of the display area is converted to interconnect wiring/traces.

For example, to individually connect to or address every emissive pixel in an array with x rows and y columns requires connections amounting to the product of x and y. If the reported deep-brain-penetrating implant is a parallel linear array of four LEDs, for example, with a common cathode and anode connection, to activate each pixel individually, the anode connection must be split into four separate leads. However, the typical minimum metal trace pitch for high density flex printed circuit boards (PCBs) is 50 µms. Adding the required additional metal traces nearly doubles the original width of the probe for just four anode connections. Thus, the flex PCB interconnect requirements to individually address even a small 32×32 discrete LED array, for example, would require 1024 separate metal interconnects, which is unmanageable from a design and manufacturing standpoint. In addition, such a device would require greater electrical power consumption from a power source placed inside the skull. It is also possible that a large number of LED's in a long-term implant would result in undesirable tissue heating.

Thus, there is a need for a system and method that selectively activates only a small subset of the overall emissive optical array. In addition, there is also a need for a system that requires less power than conventional optogenetics devices, as power consumption is directly proportional to the number of active emitting LEDs. A system that requires a decreased power consumption is also needed, such that it would be possible for a wireless inductive power source to be used, removing the expected challenges associated with supplying power from a miniature source placed inside the skull.

SUMMARY OF THE INVENTION

The present invention overcomes the aforementioned drawbacks by providing a high-resolution, untethered flexible cortical implant having an active matrix thin-film transistor (TFT) array to individually address and turn on each pixel. The TFT array uses organic light-emitting diode (OLED) display technology to optically excite neural tissue. Electronics are functionally built directly into a thin-film substrate of the TFT array, which allows individual OLED pixels in the display to be selected and turned on to target and selectively illuminate small groups of neurons. In an x by y active matrix array, connections amounting to the sum of x and y may be required, as opposed to the product of x and y as in conventional arrays. Thus, for a 32×32 array, for example, only 64 connections may be required as opposed to 1024 connections for prior art configurations.

In accordance with one aspect of the present invention, a system is disclosed for monitoring and stimulation of neural tissue in a subject. The system includes an array of microelectrodes configured to be electrically coupled to tissue of the subject and to communicate electrical signals with the tissue and an addressable array of optically emissive pixels configured to communicate with the array of microelectrodes and communicate light to the tissue. The system also includes a microelectrode circuit electrically coupled to the array of microelectrodes and configured to receive electrical signals from individual microelectrodes in the array of microelectrodes. The system further includes a pixel circuit mapped to the array of optically emissive pixels to selectively illuminate individual optically emissive elements in the array of optically emissive elements.

In accordance with another aspect of the present invention, a method is provided for monitoring and stimulating neural tissue of a subject. The method includes connecting a system for monitoring and stimulating neural tissue to a power source. The method further includes the steps of monitoring the neural tissue of the subject for a neurological event, receiving a location of electrical signals from the neural tissue of the subject, and identifying an origin of the neurological event or events based upon the location of electrical signals. The method also includes the step of delivering an optical signal to the origin of the neurological event to relieve the neurological event.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 2 is a schematic view of an example optogenetic probe for stimulating neural tissue of a subject.

DETAILED DESCRIPTION OF THE INVENTION

Figure 1A:
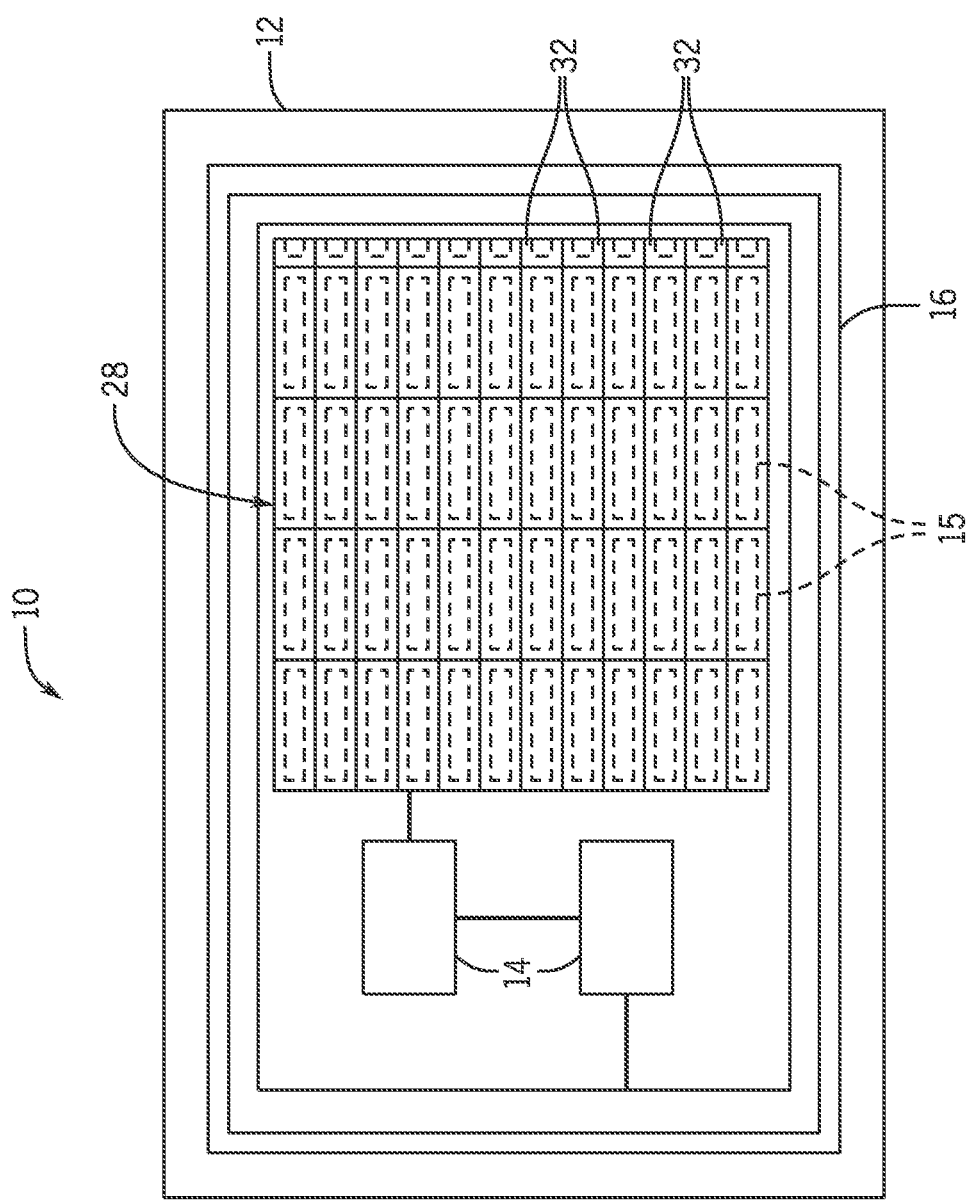
FIG. 1A is a schematic of an example organic light-emitting diode (OLED) pixel array.
Figure 1B:
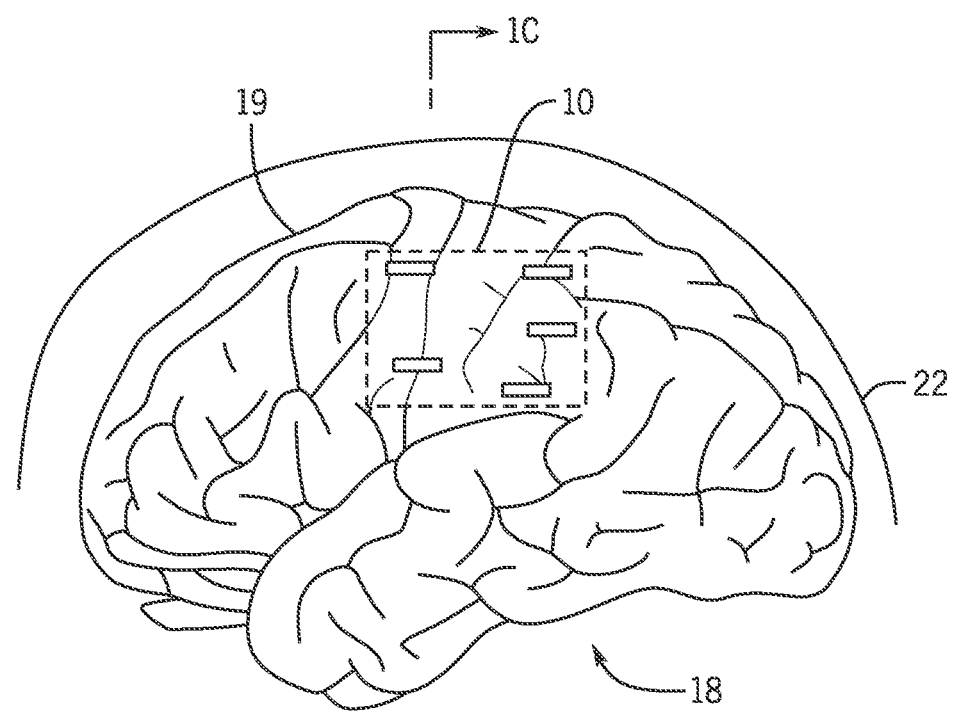
FIG. 1B is a side perspective view showing a neural stimulator provided on a brain.

Referring now to FIG. 1B, possible placement of a neural stimulator 10 on a brain 18 is shown. The neural stimulator 10 includes a biocompatible substrate 12, complementary metal-oxide-semiconductor (CMOS) neural chips 14, and an integrated inductor 16, as shown in FIG. 1A. The biocompatible substrate 12 may include an optically emissive pixel array 28, for example a, organic light-emitting diode (OLED) pixel array, having a plurality of dual-mode pixels 32. Each of the dual-mode pixels 32 can be integrated with a transparent cortical surface microelectrode 15. In one non-limiting example, the pixel array 28 may be electrically addressable and may be a blue pixel array. The CMOS neural chips 14 may be bonded to the biocompatible substrate 12 for sensor interface and stimulation, power conversion, and telemetry. The integrated inductor 16 may be configured to wirelessly transfer power.

Figure 1C:
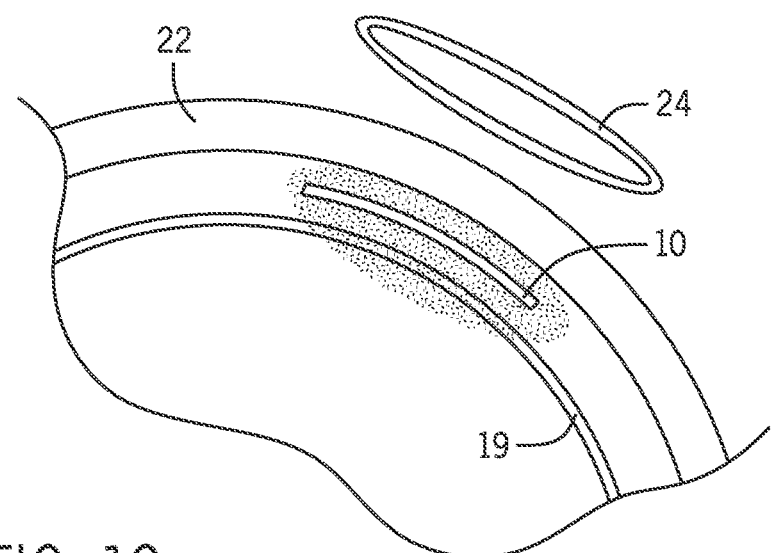
FIG. 1C is a cross-sectional view of the neural stimulator provided on the brain taken along line 1C-1C of FIG. 1B.

Referring to FIGS. 1B and 1C, the neural stimulator 10 is placed on neural tissue of a subject, for example a cortical surface 19 of the brain 18 between the brain 18 and a skull 22. A power supply 24, for example a telemetry link, may be coupled to the neural stimulator 10 by means of the integrated inductor 16. The power supply 24 can be used to provide power to a microelectrode circuit 300 and a pixel circuit 70, allowing for operation of the neural stimulator 10. The microelectrode circuit 300 and the pixel circuit 70 are described in further detail below. In some embodiments, the power supply 24 may be a wireless inductive power transfer and radio frequency link.

In an alternative embodiment, an optogenetic probe 100, for example a deep brain optogenetic probe, as shown in FIG. 2, may be used in place of the neural stimulator 10. Instead of placing the neural stimulator 10 on the cortical surface 19 of the brain 18, the optogenetic probe 100 is placed deep within the brain 18, providing stimulation below the cortical surface 19, as will be described in further detail below.

Figure 3A:
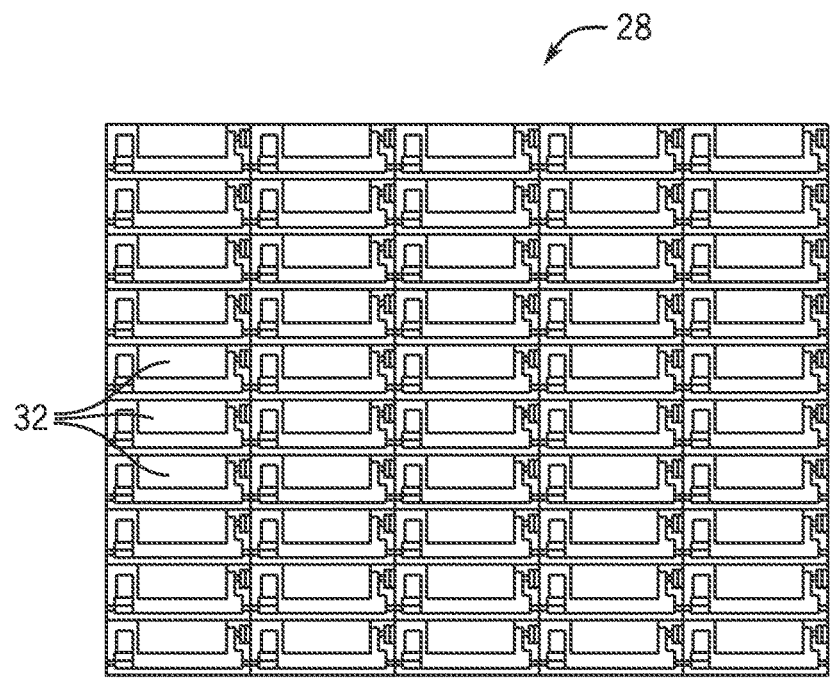
FIG. 3A is a perspective view of an pixel array.
Figure 3B:
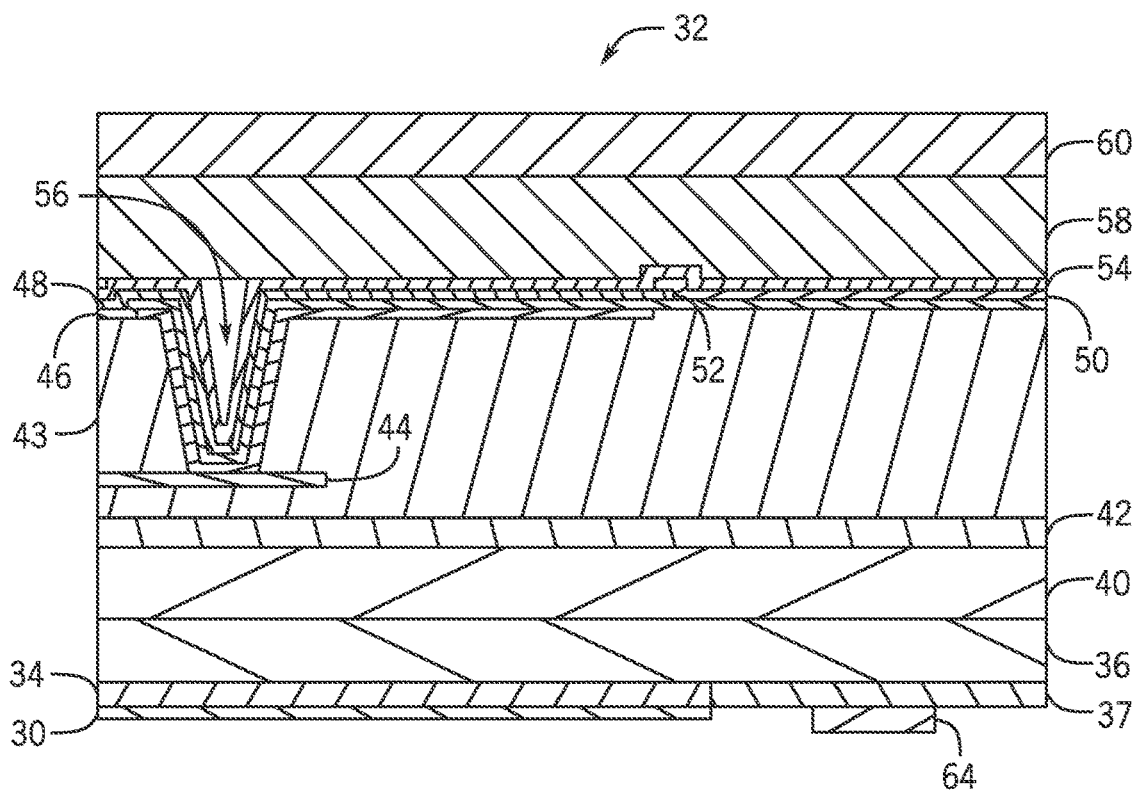
FIG. 3B is a cross-sectional view of a dual-mode pixel from the pixel array of FIG. 3A.

Referring now to FIGS. 3A and 3B, a perspective view of the pixel array 28 and a cross-sectional view of the dual-mode pixel 32 are shown. In one embodiment, as shown in FIG. 3A, the pixel array 28 includes a plurality of recording dual-mode pixels 32, however, this implementation and the associated components are non-limiting as other configurations are contemplated. For example, it is possible for the dual-mode pixels 32 to be OLED pixels, and even further to be blue OLEDs. As shown in FIG. 3B, the dual-mode pixel 32 may include a bottom-emitting, flexible OLED 64, however, other configurations, including those that incorporate top-emitting OLEDS are within the scope of the disclosure.

As shown in FIG. 3B, a cross section of the recording dual-mode pixel 32 is shown. The dual-mode pixel 32 has a backside of a first substrate 40, the bottom-emitting, flexible OLED 64 bonded using optically clear adhesive to a second substrate 36, and an indium tin oxide (ITO) microelectrode 34. In one non-limiting example, the first substrate 40 includes a polyethylene napthalate (PEN) OLED substrate, and the second substrate 36 includes a transparent PEN electrode substrate. In other embodiments, a single flexible substrate may be provided in place of the second substrate 36 bonded to the first substrate 40. The ITO microelectrode 34 may be pitch-matched to the OLED 64. A passivation layer 30 covers and electrically insulates a portion of the surface of the ITO microelectrode 34, and an exposed portion of the ITO microelectrode 34 creates a cortical surface microelectrode array (MEA) electrode 37 which mates to the cortical surface 19.

The bottom emitting flexible OLED 64 includes the first substrate 40 with a first moisture barrier 42. Positioned adjacent the first moisture barrier 42 are OLED thin film layers including an interlayer dialectic (ILD) layer 43 and an OLED anode 44, which can be coupled to a source-follower TFT 74 (see FIG. 4). An electrode layer 46, for example a transparent ITO electrode layer, is provided above the OLED anode 44. A second passivation layer 48 may be positioned above the second ITO electrode layer 46. An OLED organic layer 50 is also layered above the second ITO electrode layer 46, such that the second passivation layer 48 is discontinued at a transition point 52 and the OLED organic layer 50 begins at the transition point 52. A reflective cathode 54 may be positioned above the second passivation layer 48 and the OLED organic layer 50.

With continued reference to FIG. 3B, a via 56 is formed in the dual-mode pixel 32 between the reflective cathode 54 and a second moisture barrier 58 positioned above the reflective cathode 54. In one example, the via 56 may be substantially tapered in shape and positioned in a section of the dual-mode pixel 32 with the second passivation layer 48 as opposed to a section of the dual-mode pixel 32 with the OLED organic layer 50 However, the via 56 may be characterized by other shapes, such as a rectangle, pyramid, or arc.

The dual-mode pixel 32 may further include a heat sink 60 positioned above the second moisture barrier 58. The heat sink 60 may be a foil, for example, that dissipates heat as part of a heat management system. Although the cross sectional view of FIG. 3B does not show thin film layers used to construct a control thin-film transistor (TFT) 72, a source-follower TFT 74, and a capacitor 76, the aforementioned elements are shown in the circuit schematic of the dual-mode pixel 32 of FIG. 4A. The control TFT 72 and the source-follower TFT 74 each have a source terminal 78, a gate terminal 80, and a drain terminal 82. The control TFT 72 and the source-follower TFT 74 are discussed in greater detail below. The heat management system may also include an energy storage device configured to pulse the current to produce less heat instead of applying steady current.

Figure 4A:
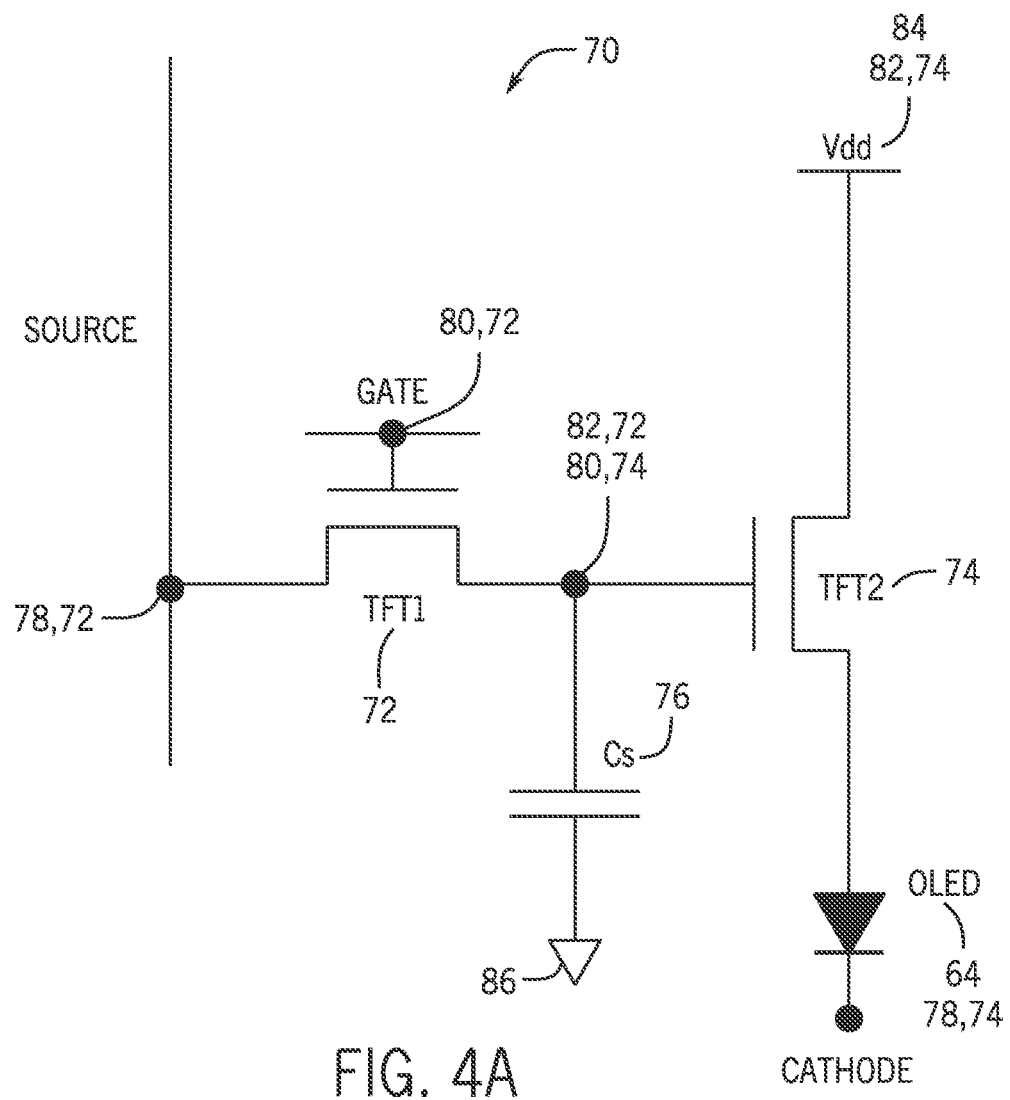
FIG. 4A is an example schematic of a circuit of the dual-mode pixel of FIG. 3B.

As shown in FIG. 4A, a schematic of a pixel circuit 70 for an OLED portion of the dual-mode pixel 32 of FIG. 3A is shown. The pixel circuit 70 for the dual-mode pixel 32 includes two TFTs comprising the control TFT 72, the source-follower TFT 74, the capacitor 76, a Voltage Drain Drain (VDD) voltage source 84, and the OLED 64. The control TFT 72 is shown open at the source terminal 78 and the gate terminal 80 so as to simulate a connection to another OLED pixel in the pixel array 28. The capacitor 76 is coupled between the drain terminal 82 of control TFT 72 and ground 86. The gate terminal 80 of the source-follower TFT 74 may also be coupled to the drain terminal 82 of the control TFT 72. The drain terminal 82 of the source-follower TFT 74 is coupled to the VDD voltage source 84, and the OLED 64 is connected to the source terminal 78 of the source-follower TFT2 74.

The dual-mode pixel 32 may be configured to deliver light simultaneously from the OLED 64 with the electrophysiological recording of biopotentials by the neural stimulator 10 from optically stimulated neural tissue. Neurological events, such as seizures, can be monitored for, and individual dual-mode pixels 32 can be illuminated to relieve the neurological event. Since the light delivery can be localized by turning on individual dual-mode pixels 32 in the pixel array 28 for precise spatial and temporal control, isolated neurological events can be monitored and recorded, while the neural tissue is being optically stimulated using the dual-mode pixel 32 configuration. Additionally, since applying pulsed blue light only activates cells expressing ChR2, it is advantageous to also be able to deliver pulsed yellow light to cells that express Halorhodospin to quiet or silence the cells. This leads to an alternate optogenetics pixel configuration where dual-mode pixels 32 emit multiple colors that provide both localized, addressable optical activation and silencing of neural activity.

Turning again to FIG. 2, in the presence of the optogenetic probe 100, the configuration of the pixel array 128 may be comparable to the pixel array 28 illustrated in FIG. 2, but on a substantially smaller scale. In some embodiments, at a lower resolution, a thin sliver of the same pixel array 128 could be employed. Power transfer and control interface electronics 104, which may be small, thin disks, can be attached to an end 102 of the optogenetic probe 100 and placed directly underneath the skull 22. Similar to the pixel array 128, the interface electronics 104 may be integrated on a flexible substrate 112 also integrated with pixel array 128.

Figure 4B:
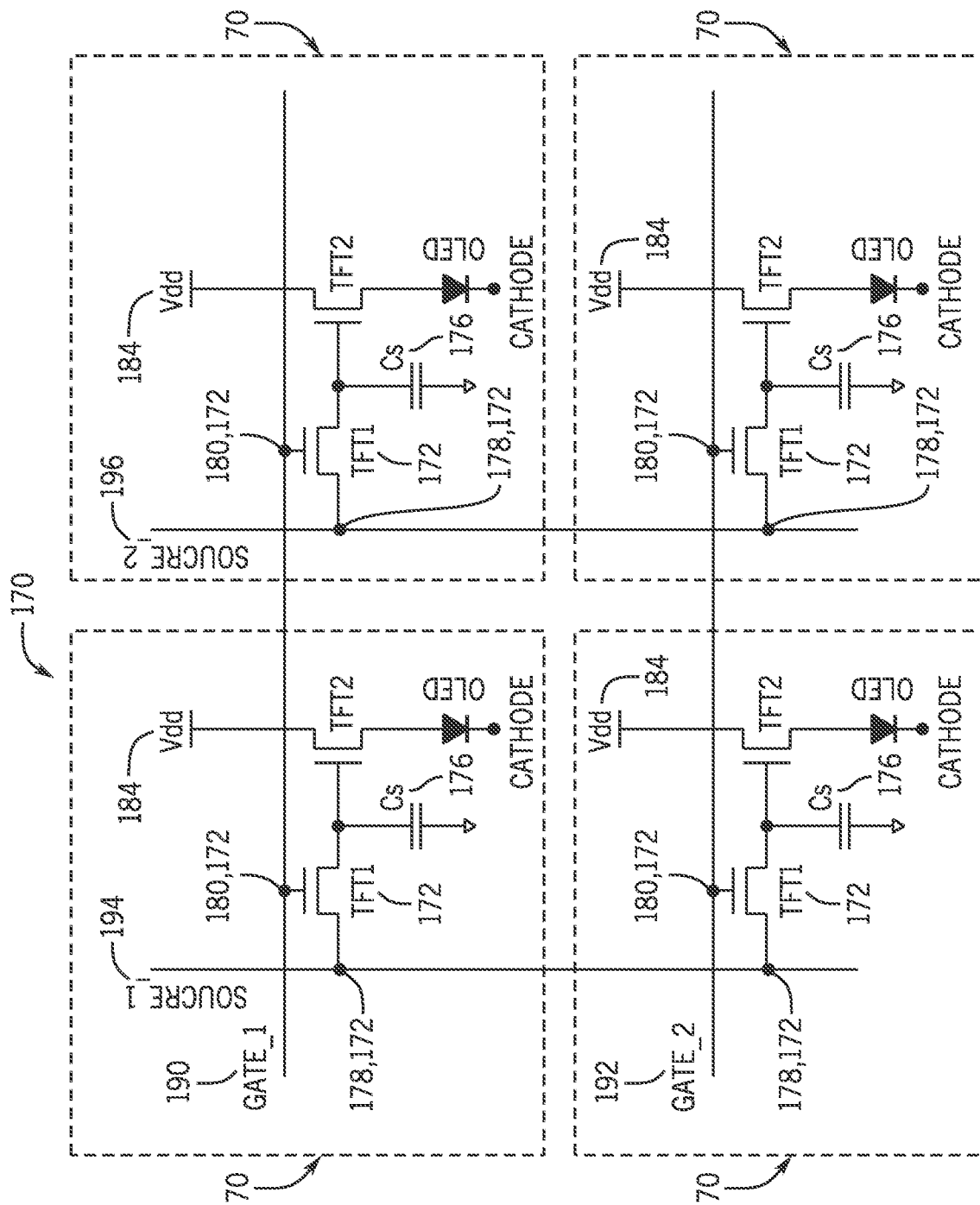
FIG. 4B is an example schematic of a circuit of a TFT active pixel circuit.
Figure 5:
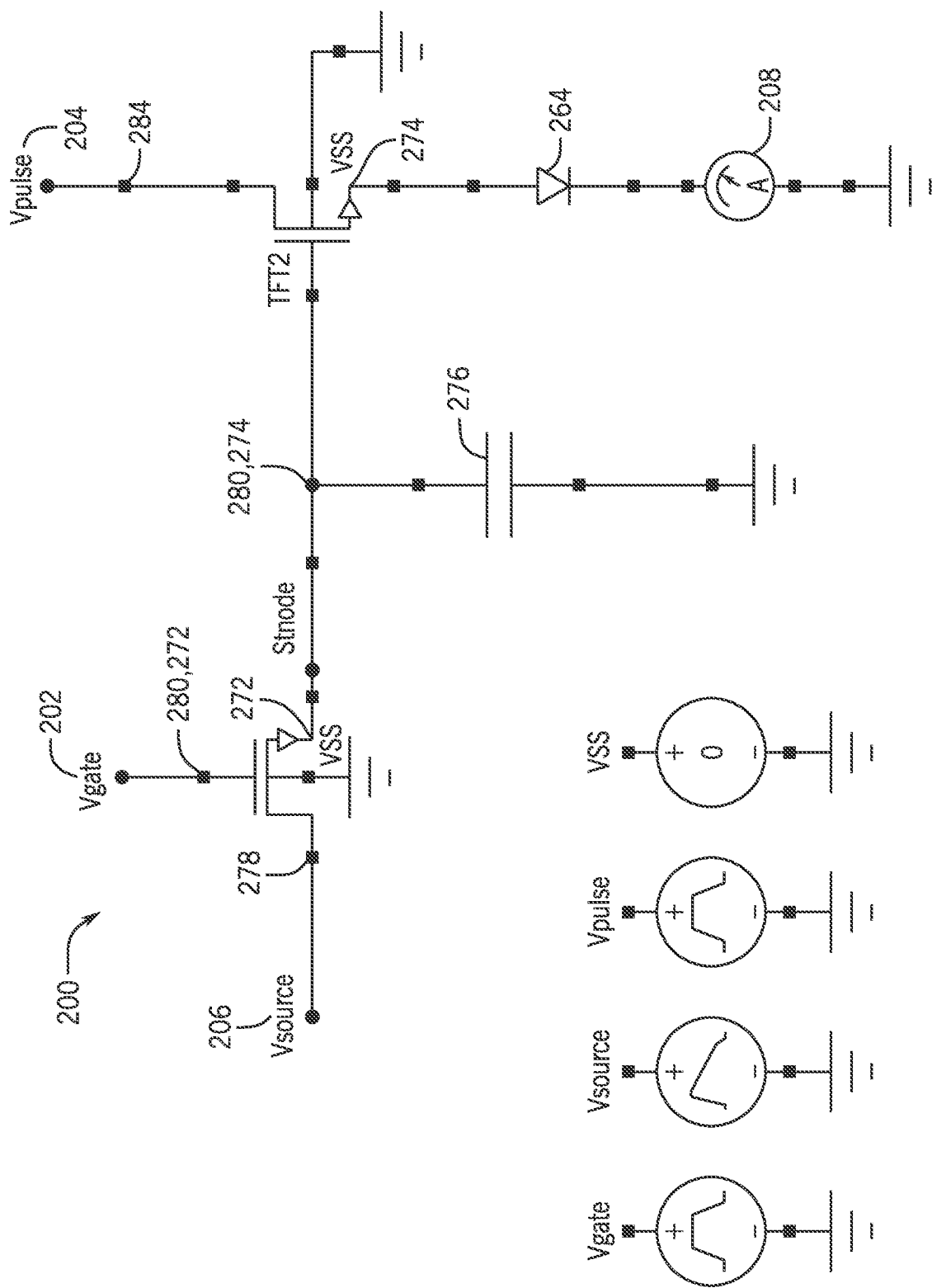
FIG. 5 is a schematic of a circuit for the dual-mode pixel.

Referring now to FIG. 4B, an example schematic of a TFT active pixel sensor circuit 170 is shown. The TFT active pixel sensor circuit 170 includes four OLED pixel circuits 70 for the dual-mode pixel 32 shown in FIG. 2. The four OLED pixel circuits 70 are interconnected via the source terminal 178 and the gate terminal 180 of the control TFT 172 such that the control TFT 172 gates in each individual gate line (i.e., Gate_1 190 and Gate_2 192) are connected together and the control TFT 172 sources in each individual source line (i.e., Source_1 194 and Source_2 196) are connected together. As shown in FIG. 5, a circuit schematic 200 for a circuit for the dual-mode pixel 32 is shown. The circuit schematic 200 shows a gate voltage 202 at the gate terminal 280, a pulsed supply voltage 204 which is coupled to the VDD voltage source 284, a source voltage 206 at the source terminal 278, and an OLED current 208 through the OLED 264.

The emitted light intensity or luminance of the dual-mode pixel 32 may be current-controlled. Thus, the TFT current source for the dual-mode pixel 32 is configured to pulse on and off. In pulsed operation, as illustrated by the circuit schematic 200, the gate voltage 202 is first applied to the gate terminal 280 of control TFT 272, turning control TFT 272 on. This transfers the source voltage 206 to the capacitor 276 where the source voltage 206 is stored. The control TFT 272 is then switched off, (e.g., gate goes low at 13 ms), and the source voltage 206 stored on the capacitor 276 may be available to the gate terminal 280 of source follower TFT 274.

In one example, the TFT active pixel sensor circuit 170 may be configured in pulsed mode such that while writing the active pixel array 28, the (VDD) voltage source 184 is turned off, consequently turning off the source-follower TFT 174. By turning off the source-follower TFT 174, the OLED 64 is inhibited from turning on (i.e., lighting up). After the pixel array 28 is written by sequentially addressing individual gate lines 190 and 192, the VDD voltage source 184 is turned on, for example at 15 ms. Dual-mode pixels 32 with a voltage stored on the capacitor 176 are also turned on. Dual-mode pixels 32 without a voltage stored on the capacitor 176 (e.g., 0 volts) are not turned on. This sequential operation may provide the ability to both individually address (i.e., write to) dual-mode pixels 32 in the pixel array 28, as well as support the required pulsed mode operation.

Referring again to the circuit schematic 200 of FIG. 5, the dual-mode pixel 32 may turn off again after the supply voltage is pulsed off, for example at 23 ms. At an array level, pulsing the supply voltage off corresponds to the beginning of another write cycle to the pixel array 28. The timing sequence may be repeated with 0 volts (off state) from the source-follower TFT 274 written onto the capacitor 276. When the VDD voltage source 284 is pulsed on again at 35 ms, for example, there is no current flowing through the dual-mode pixel 32. Thus, the dual-mode pixel 32 is off and does not light up.

Figure 6:
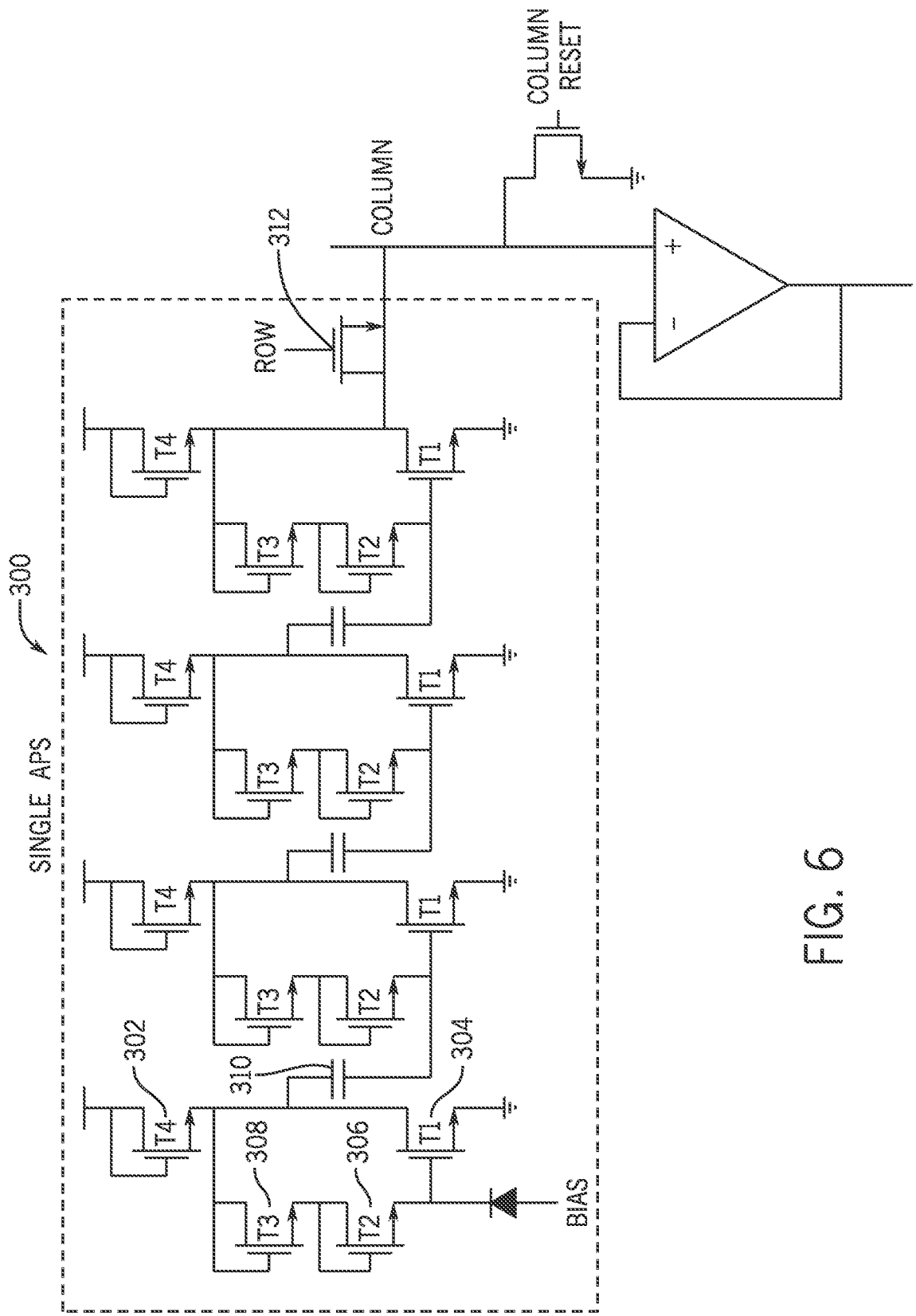
FIG. 6 is an example schematic of an integrated low noise active pixel sensor (APS) circuit.

Referring now to FIG. 6, an example schematic of a microelectrode circuit 300 is shown. At the pixel level, the transparent ITO microelectrode 34 of FIG. 3B may be connected to the microelectrode circuit 300. The microelectrode circuit 300 may be addressed using peripheral TFT based logic for random access and reading of electrical activity in neural tissue from the individual ITO microelectrodes 34 (see FIG. 3B). The ITO microelectrodes 34 may be capacitively coupled to a cellular membrane surface. Thus, the extra-cellular surface ITO microelectrodes 34 can directly detect a biopotential representative of a change in internal cellular action potentials corresponding to ion channel currents in the cellular membrane. The microelectrode circuit 300 may be integrated within each pixel of the pixel array 28.

The four-stage microelectrode circuit 300 shown in FIG. 6 is an example of an APS circuit used to detect the short duration pulses that occur during alpha strikes. In one non-limiting example, the microelectrode circuit 300 may be implemented using N-type only Indium-Gallium-Zinc-Oxide (IGZO) TFTs on a polyethylene naphthalate plastic substrate. Configured as an alpha particle detector, the microelectrode circuit 300 provides a gain of about 20-30 $V_{out}/V_{in}$, and reliably detects the small electrical impulses at the input sensitive node from incident alpha particles emitted from a $^{210}$Po alpha source (not shown). Thus, the microelectrode circuit 300 exhibits a multi-staged behavior by using multiple low-power Common Source (CS) amplification stages comprising a first common source amplification TFT 302 and a second common source amplification TFT 304. Each stage is self-biased in the DC regime via a first diode-connected TFT 306 coupled to a second diode-connected TFT 308. Following a small change in voltage at the sensitive node input, the self-biasing enables the microelectrode circuit 300 to reset to a high-gain state. The output of the CS stage is then connected via an AC coupling capacitor 310 to the input of the next CS amplification stage, which is simply a copy of the first stage. The AC coupling capacitor 310 permits the input of the subsequent stage to have the correct DC bias, while still passing the high frequency pulse expected from an almost instantaneous change in charge at the sensitive node.

The output of the final CS stage can be directly fed into the array column output, via a row access transistor 312. Thus, during array readout, the columns of each row are read out independently. In other words, following a read, each column may be reset to a lower voltage (e.g., 0V) before the next row is accessed. This reduces the remaining voltage from the column output which could affect the operation of the pixels in the next row.

Figure 7A:
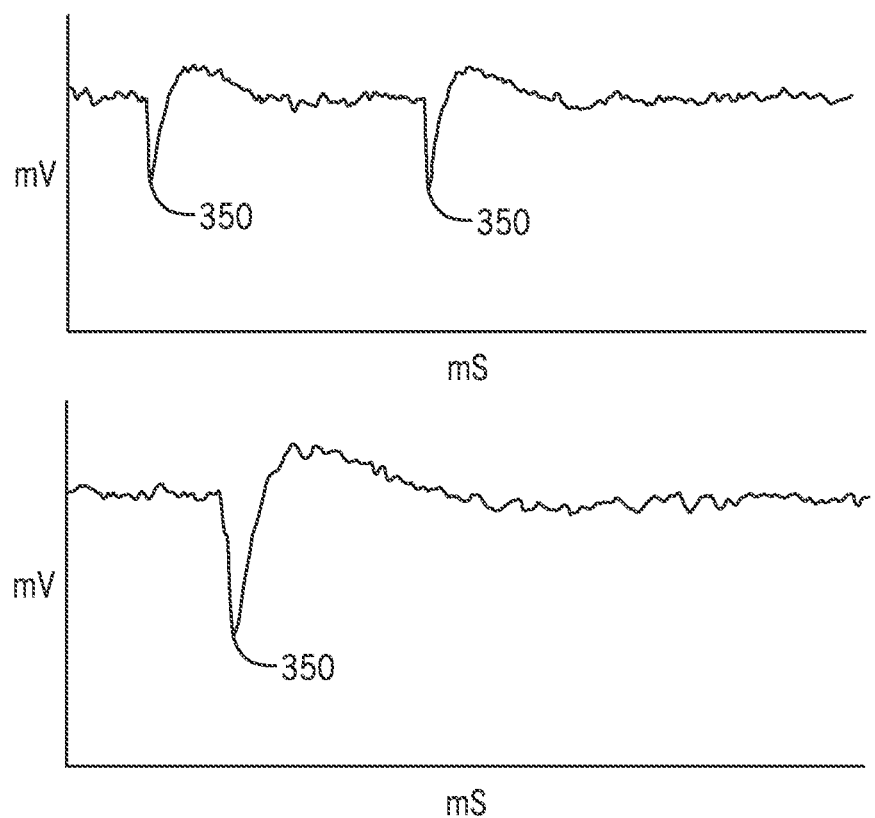
FIG. 7A shows charts of alpha induced pulses measured at an output of a four-stage APS circuit.
Figure 7B:
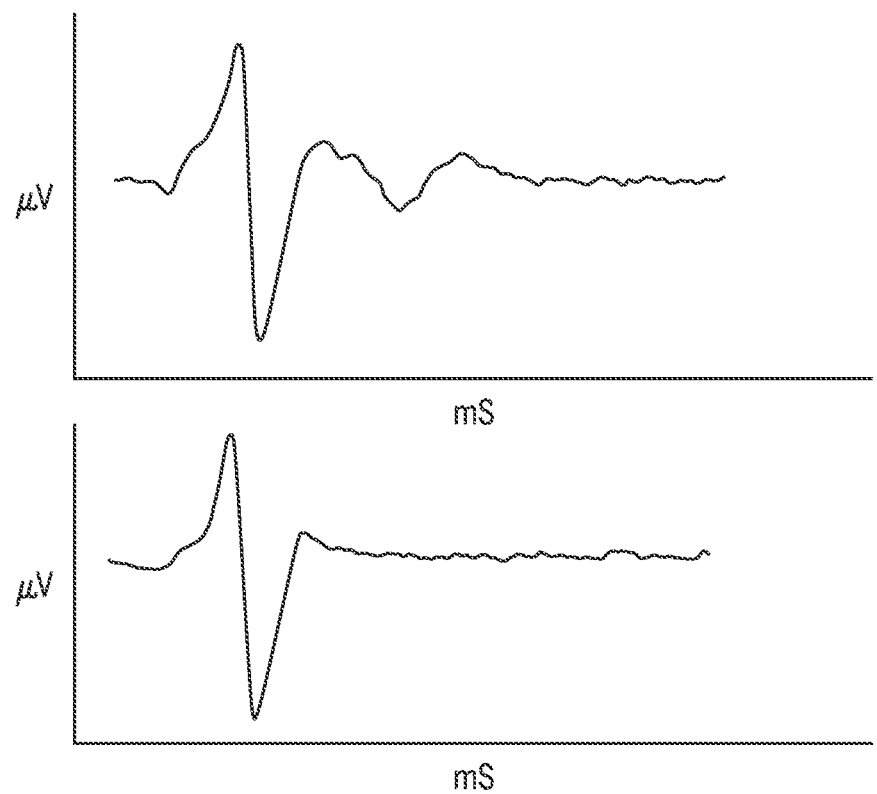
FIG. 7B shows charts biopotential pulses detected from neural activity.

Referring now to FIG. 7A, graphs detailing alpha induced pulses 350 measured at the output of a four-stage microelectrode circuit, such as the circuit 300 of FIG. 6, are shown. In operation, the microelectrode circuit 300 may capture activity that identifies both the precise array location, as well as electrophysiology of the detected neural activity. Analogous to the small impulse detection of individual firing neurons, is the detection of individual alpha particle strikes within a PIN diode. Thus, existing APS circuits may be leveraged to detect similar impulse-like neural activity. In the case of the neural impulse detector, however, the PIN diode is may be replaced by the ITO microelectrode 34 of FIG. 3B connected to the APS input. The ITO microelectrode 34 then contacts the cortical surface 19, shown in FIGS. 1B and 1C, and registers the action potential of a neural pulse. Example readings of a biopotential pulse detected from neural activity are shown in FIG. 7B.

Figure 8A:
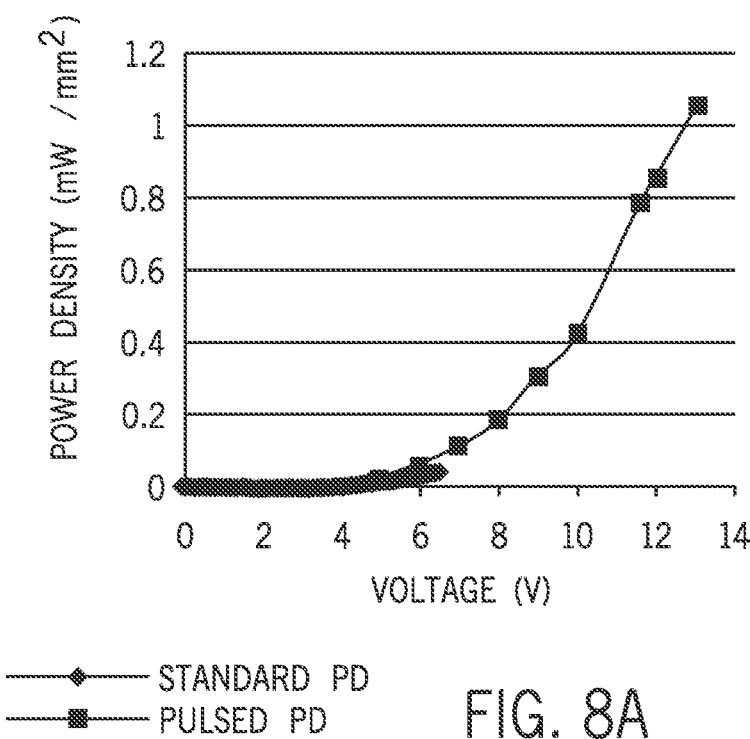
FIG. 8A is a graph of measured light emission intensity for dual-mode pixels under continuous and pulsed mode operation.
Figure 8B:
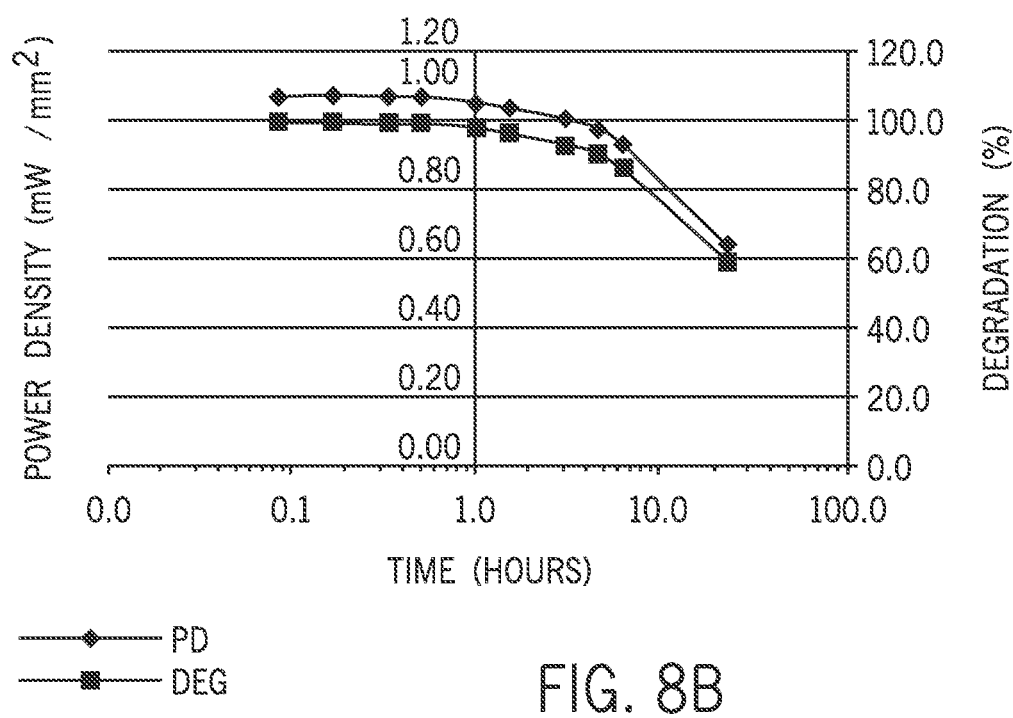
FIG. 8B is a graph of long term stability of dual-mode pixels under 1 mW/mm$^2$ pulsed mode operation.

Referring now to FIG. 8A, a chart of measured light emission intensity for flexible 455 nm blue OLEDs, for example, under standard and pulsed mode operation is shown. In one example, the pulsed mode is a 1 mW/mm² pulsed operation. The intensity of 1 mW/mm² is about 10× greater than the intensity of 0.1 mW/mm² observed from a conventional OLED biased at 7V DC, which is a typical bias condition for a commercial flat panel OLED display. Similar to a semiconductor diode, increasing the voltage across an OLED exponentially increases the current. This causes the OLED light intensity to increase exponentially, as well. However, increasing the static DC bias above a threshold, for example 7V, to obtain higher intensity begins to degrade the OLED organic emission layers, as shown in the graph of FIG. 8B. The degradation of the OLED can be attributed to current-induced localized joule heating in the OLED organic layers. However, by pulsing the bias supply (the VDD voltage source 84 of FIG. 4A), the OLED operating voltage can be increased and subsequently increase the instantaneous light intensity to the desired output without degrading or damaging the OLED. Keeping the pulse width short, and operating at a low frequency, gives the organic layers in the OLED a chance to recover and cool down before applying a voltage bias in the next period. Essentially, the OLED can be operated until a temperature of the OLED increases. Operation of the OLED is then terminated, allowing the temperature of the OLED to decrease before operation continues.

In one example, the 1 mW/mm2 of instantaneous light intensity at 455 nm may be achieved using a 13 volt, 20 Hz pulse with a 10 ms pulse width. Pulsing the supply voltage aligns with the reported 20 Hz pulsed operation conditions used to drive discrete LEDs in optogenetic applications. Additionally, the long-term stability of a 455 nm blue OLED on a PEN plastic substrate may be evaluated under 1 mW/mm² continuous pulsed operational conditions. Reasonable stability can be observed after 20 hours, with a $t_{90}$ at approximately 6 to 7 hours. To remove the heat generated during pulsed operation, a 30 μm thick flexible metal foil layer, for example, may be bonded to the cathode side of the dual-mode pixel 32, shown as the heat sink 60 in FIG. 3B. In absence of the thin metal foil heat sink 60, dual-mode pixels 32 on the first substrate 40 may degrade under pulsed (1 mW/mm²) operating conditions.

Figure 9:
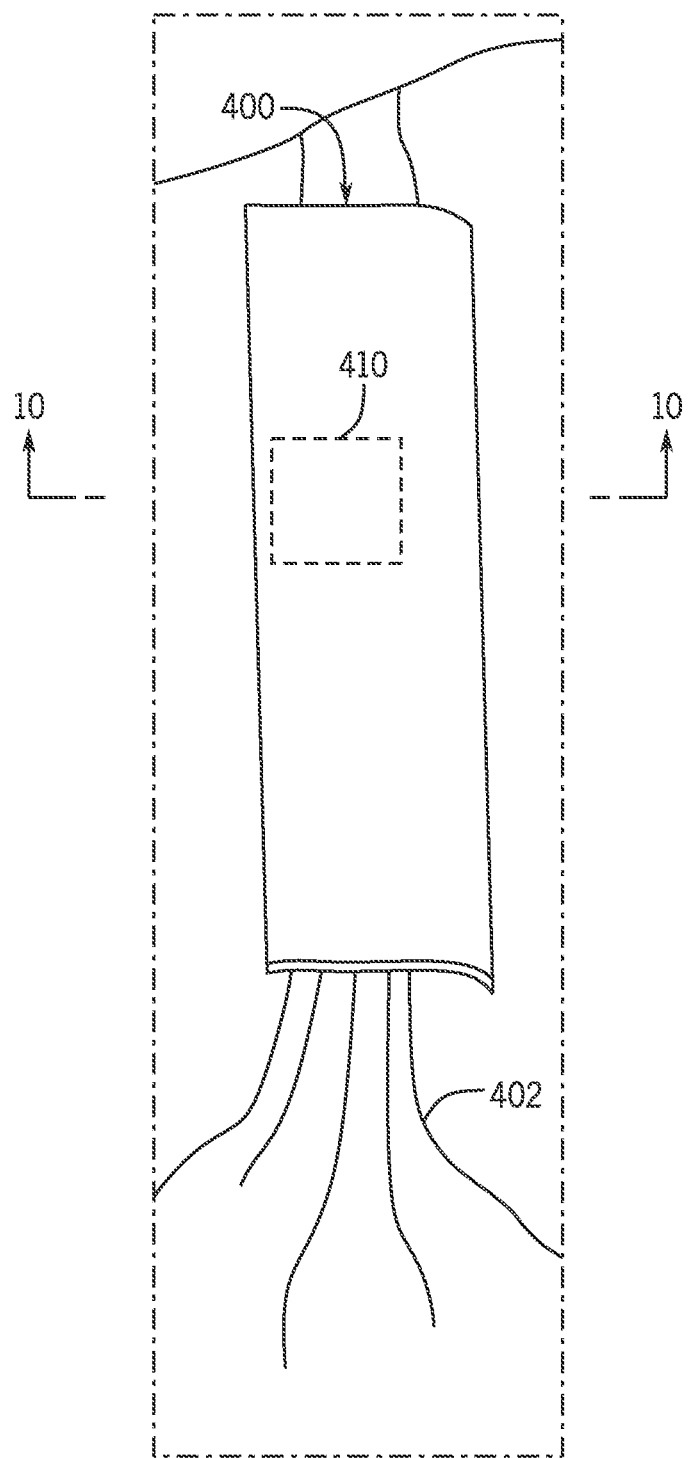
FIG. 9 is a perspective view showing one embodiment of a neural cuff coupled to a nerve.

In addition to stimulating the cortical surface 19, the neural stimulator 10 may be to be used to stimulate isolated groups of neurons in the peripheral nervous system. As shown in FIG. 9, a neural stimulator 410 is integrated with a neural cuff 400, and can be wrapped around a nerve 402, such as the sciatic nerve, to allow for the monitoring of neuronal electrical activity. In this embodiment, the neural cuff 400 enables localized micro-electroporation to allow targeted delivery of designer plasmids. This capability can enable localized gene modulation for gene therapeutic approaches to act in tandem with neuronal stimulation.

Figure 10:
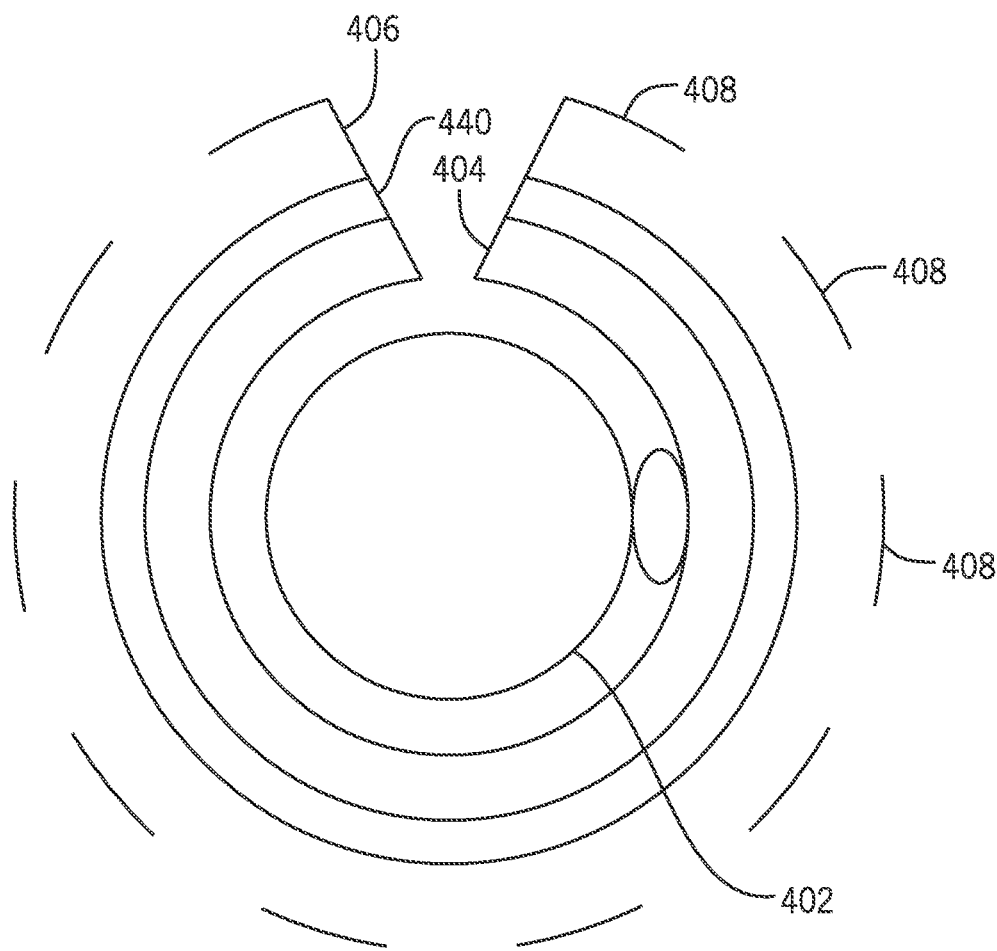
FIG. 10 is a cross sectional view of the neural cuff and nerve of FIG. 9 taken along line 10-10.

In one embodiment of the neural cuff 400, an inner neuron-facing OLED display layer 404, and a separate outward facing biosensor array layer 406 are implemented as illustrated in FIG. 10. Both the neuron-facing OLED display layer 404 and the biosensor array layer 406 may be manufactured on a thin and flexible plastic substrate 440, such as polyimide. Furthermore, two back-to-back layers provide inherent self-encapsulation, which is beneficial for chronic in vivo applications. Internal control functions and external interfacing can be accomplished by bonding CMOS integrated circuits 408 to the biosensor array layer 406. Given its coiled shape, the neural cuff 400 lends itself to internally routing a metal interconnect trace throughout the neural cuff 400 in the shape of a coil for wireless inductive power transfer. An external electronics assembly can be placed on the surface of a patient's (not shown) skin near the implanted neural cuff 400, providing power to the neural cuff 400 via inductive power transfer. Additionally, the external electronics may provide radio-frequency (RF) monitoring and control signals, which can be detected by the CMOS integrated circuits 408.

Figure 11:
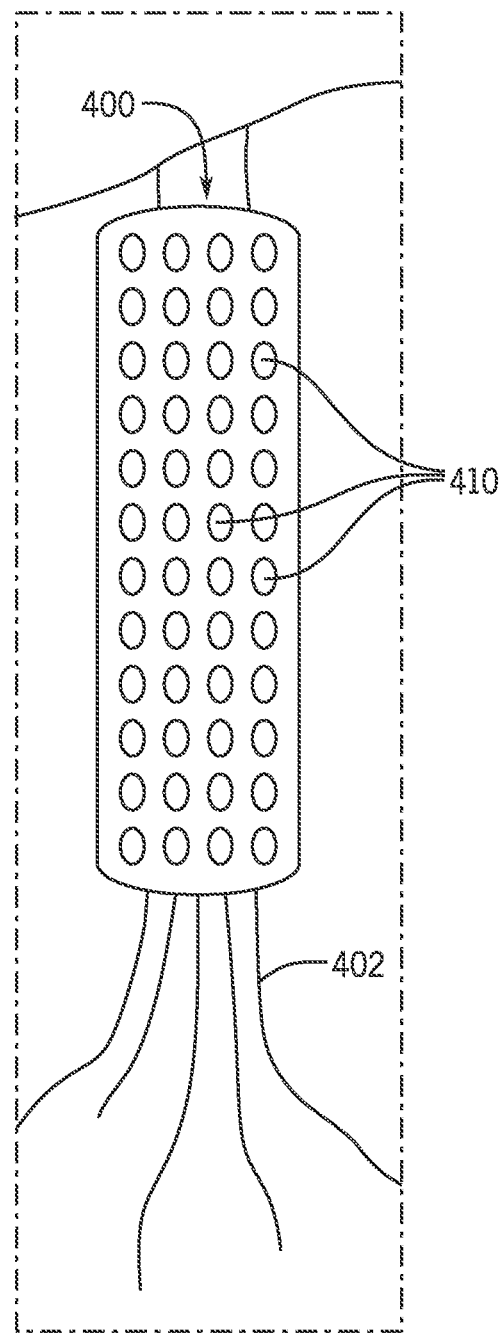
FIG. 11 is a perspective view showing an additional embodiment of a neural cuff.

In one embodiment, the neural cuff 400 may be used to detect pain-related protein biomarkers in vivo. An immunoassay can be used to provide a reasonable probability of detection. In this embodiment, the neural cuff 400 is integrated with an array of individual thin-film biosensors 410, for example Ion-Sensitive Field Effect Transistor (ISFET) pH biosensors, as shown in FIG. 11. The individual biosensors 410 can be sequentially activated to provide near-continuous biomarker detection.

In one example, an aperture covering or sealing the active surface for each individual immunosensor in the array can be chemically or electrically opened. At the completion of a biomarker concentration measurement, the next aperture can be opened over an unused (fresh) biosensor 410 in the array, using a preset sample interval. The action of sequentially opening a new aperture over each biosensor 410 in a large multi-biosensor array, as opposed to using a single biosensor over the life of the implant, can mitigate the effects of surface biofouling and enhance the stability of the biosensors. In addition, miniaturized fluorescence measurements using a flexible OLED display and hydrogenated amorphous silicon (a-Si:H) PiN photodiode active matrix array technology can allow for point-of-use diagnosis of multiple disease or pathogen markers by performing an ELISA-type immunoassay.

The present invention has been described in terms of one or more preferred embodiments, and it should be appreciated that many equivalents, alternatives, variations, and modifications, aside from those expressly stated, are possible and within the scope of the invention.

We claim:

1. A system for monitoring and stimulating tissue in a subject, the system comprising:
an array of microelectrodes electrically configured to couple to the tissue of the subject and configured to communicate electrical signals with the tissue;
an addressable array of optically emissive pixels configured to communicate with the array of microelectrodes and to communicate light to the tissue;
a microelectrode circuit electrically coupled to the array of microelectrodes and configured to receive electrical signals from individual microelectrodes in the array of microelectrodes; and
a pixel circuit mapped to the array of optically emissive pixels to selectively illuminate individual optically emissive pixels in the array of optically emissive pixels, wherein the pixel circuit comprises a plurality of pixel subcircuits, each pixel subcircuit comprising a first transistor and a second transistor, the first transistor comprising a first transistor first terminal, a first transistor second terminal, and a first transistor gate terminal, the second transistor comprising a second transistor first terminal, a second transistor second terminal, and a second transistor gate terminal, the first transistor gate terminal coupled to a gate input, the first transistor first terminal coupled to a source input, the first transistor second terminal coupled to the second transistor gate terminal, the second transistor first terminal coupled to a voltage source, the second transistor second terminal coupled to one of the optically emissive pixels, wherein the source input is coupled to a second pixel subcircuit and the gate input is coupled to a third pixel subcircuit.

2. The system of claim 1 further comprising a substrate supporting at least one of the array of microelectrodes, the microelectrode circuit, the pixel circuit, and the addressable array of optically emissive pixels.

3. The system of claim 2 further comprising an inductor supported by the substrate and configured to provide operational power to at least one of the array of microelectrodes, the microelectrode circuit, the pixel circuit, and the addressable array of optically emissive pixels.

4. The system of claim 3 further comprising a wireless power supply in communication with the indicator and configured to provide power to the microelectrode circuit and the pixel circuit.

5. The system of claim 1 further comprising a heat sink configured to control a temperature of at least one of the array of microelectrodes, the microelectrode control circuit, the optically emissive element control circuit, and the addressable array of optically emissive elements.

6. The system of claim 5 wherein the heat sink includes a heat dissipation foil.

7. The system of claim 1, wherein the optically emissive pixels are flexible organic light-emitting diodes.

8. The system of claim 1 wherein the tissue is a cortical surface of the brain and the array of microelectrodes is configured to capacitively couple to the cortical surface of the brain.

9. The system of claim 1 wherein the system forms a neural cuff, the neural cuff configured to be in contact with the tissue.

10. The system of claim 9 wherein the tissue is a nerve of the subject.

11. The system of claim 9 further including an array of biosensors configured to detect pain-related protein biomarkers.

12. The system of claim 1 wherein the array of emissive pixels comprises at least one of blue pixels and yellow pixels.

13. The system of claim 12 wherein the blue pixels communicate with cells expressing Channelrhodopsin and the yellow pixels communicate with cells expressing Halorhodospin.

* * * * *